(12) United States Patent
Chanduszko et al.

(10) Patent No.: US 7,842,053 B2
(45) Date of Patent: Nov. 30, 2010

(54) DOUBLE COIL OCCLUDER

(75) Inventors: Andrzej J. Chanduszko, Chandler, AZ (US); David R. Widomski, Wakefield, MA (US)

(73) Assignee: NMT Medical, Inc., Boston, MA (US)

( * ) Notice: Subject to any disclaimer, the term of this patent is extended or adjusted under 35 U.S.C. 154(b) by 314 days.

(21) Appl. No.: 11/093,348

(22) Filed: Mar. 30, 2005

(65) Prior Publication Data

US 2005/0251154 A1    Nov. 10, 2005

Related U.S. Application Data

(60) Provisional application No. 60/568,526, filed on May 6, 2004.

(51) Int. Cl.
*A61B 17/08* (2006.01)
(52) U.S. Cl. .................................................. 606/157
(58) Field of Classification Search ................ 606/215, 606/139, 151, 157, 159, 213, 232; 623/3.1
See application file for complete search history.

(56) References Cited

U.S. PATENT DOCUMENTS

| | | | |
|---|---|---|---|
| 3,344,048 A | 9/1967 | Kobetz et al. |
| 3,824,631 A | 7/1974 | Burstein et al. |
| 3,874,388 A | 4/1975 | King et al. |
| 3,875,648 A | 4/1975 | Bone |
| 3,924,631 A | 12/1975 | Mancusi, Jr. |
| 4,006,747 A | 2/1977 | Kronenthal et al. |
| 4,007,743 A | 2/1977 | Blake |
| 4,149,327 A | 4/1979 | Hammer et al. |
| 4,425,908 A | 1/1984 | Simon |
| 4,610,674 A | 9/1986 | Suzuki et al. |
| 4,626,245 A | 12/1986 | Weinstein |
| 4,693,249 A | 9/1987 | Schenck et al. |
| 4,696,300 A | 9/1987 | Anderson |
| 4,710,181 A | 12/1987 | Fuqua |
| 4,710,192 A | 12/1987 | Liotta et al. |
| 4,738,666 A | 4/1988 | Fuqua |
| 4,836,204 A | 6/1989 | Landymore et al. |
| 4,840,623 A | 6/1989 | Quackenbush |

(Continued)

FOREIGN PATENT DOCUMENTS

DE        9413645 U1    10/1994

(Continued)

OTHER PUBLICATIONS

Applied Fibre Science, F. Happey, Ed. Chapter 8, E. Atkins, Academic Press, New York 1979.

(Continued)

*Primary Examiner*—(Jackie) Tan-Uyen T Ho
*Assistant Examiner*—Gregory Anderson
(74) *Attorney, Agent, or Firm*—Helen S. Liu

(57) ABSTRACT

An occluder that has a coil on one or both sides of a medical defect, particularly a septal defect such as a patent foramen ovale (PFO). Each coil can be formed as a tube that is hollow, with or without a closed end. The tube can be delivered over a wire. For occluding a PFO, the coils can be designed to provide a compressive force to one or both of septum primum and septum secundum.

25 Claims, 14 Drawing Sheets

U.S. PATENT DOCUMENTS

| | | | |
|---|---|---|---|
| 4,902,508 A | 2/1990 | Badylak et al. | |
| 4,915,107 A | 4/1990 | Rebuffat et al. | |
| 4,917,089 A | 4/1990 | Sideris | |
| 4,921,479 A | 5/1990 | Grayzel | |
| 4,956,178 A | 9/1990 | Badylak et al. | |
| 5,021,059 A | 6/1991 | Kensey et al. | |
| 5,037,433 A | 8/1991 | Wilk et al. | |
| 5,041,129 A | 8/1991 | Hayhurst et al. | |
| 5,049,131 A | 9/1991 | Deuss | |
| 5,078,736 A | 1/1992 | Behl | |
| 5,106,913 A | 4/1992 | Yamaguchi et al. | |
| 5,108,420 A | 4/1992 | Marks | |
| 5,149,327 A | 9/1992 | Oshiyama | |
| 5,163,131 A | 11/1992 | Row et al. | |
| 5,167,363 A | 12/1992 | Adkinson et al. | |
| 5,167,637 A | 12/1992 | Okada et al. | |
| 5,171,259 A | 12/1992 | Inoue | |
| 5,176,659 A | 1/1993 | Mancini | |
| 5,192,301 A | 3/1993 | Kamiya et al. | |
| 5,222,974 A | 6/1993 | Kensey et al. | |
| 5,226,879 A | 7/1993 | Ensminger et al. | |
| 5,236,440 A | 8/1993 | Hlavacek | |
| 5,245,023 A | 9/1993 | Peoples et al. | |
| 5,245,080 A | 9/1993 | Aubard et al. | |
| 5,250,430 A | 10/1993 | Peoples et al. | |
| 5,257,637 A | 11/1993 | El Gazayerli | |
| 5,275,826 A | 1/1994 | Badylak et al. | |
| 5,282,827 A | 2/1994 | Kensey et al. | |
| 5,284,488 A | 2/1994 | Sideris | |
| 5,304,184 A | 4/1994 | Hathaway et al. | |
| 5,312,341 A | 5/1994 | Turi | |
| 5,312,435 A | 5/1994 | Nash et al. | |
| 5,316,262 A | 5/1994 | Koebler | |
| 5,320,611 A | 6/1994 | Bonutti et al. | |
| 5,334,217 A | 8/1994 | Das | |
| 5,350,363 A | 9/1994 | Goode et al. | |
| 5,354,308 A | 10/1994 | Simon et al. | |
| 5,364,356 A | 11/1994 | Hofling | |
| 5,411,481 A | 5/1995 | Allen et al. | |
| 5,413,584 A | 5/1995 | Schulze | |
| 5,417,699 A | 5/1995 | Klein et al. | |
| 5,425,744 A | 6/1995 | Fagan et al. | |
| 5,433,727 A | 7/1995 | Sideris | |
| 5,451,235 A | 9/1995 | Lock et al. | |
| 5,453,099 A | 9/1995 | Lee et al. | |
| 5,478,353 A | 12/1995 | Yoon | |
| 5,480,353 A | 1/1996 | Garza, Jr. | |
| 5,480,424 A | 1/1996 | Cox | |
| 5,486,193 A | 1/1996 | Bourne et al. | |
| 5,507,811 A | 4/1996 | Koike et al. | |
| 5,534,432 A | 7/1996 | Peoples et al. | |
| 5,540,712 A | 7/1996 | Kleshinski et al. | |
| 5,562,632 A | 10/1996 | Davila et al. | |
| 5,577,299 A | 11/1996 | Thompson et al. | |
| 5,601,571 A | 2/1997 | Moss | |
| 5,603,703 A | 2/1997 | Elsberry et al. | |
| 5,618,311 A | 4/1997 | Gryskiewicz | |
| 5,620,461 A | 4/1997 | Muijs Van De Moer et al. | |
| 5,626,599 A | 5/1997 | Bourne et al. | |
| 5,634,936 A | 6/1997 | Linden et al. | |
| 5,649,950 A | 7/1997 | Bourne et al. | |
| 5,649,959 A | 7/1997 | Hannam et al. | |
| 5,663,063 A | 9/1997 | Peoples et al. | |
| 5,683,411 A | 11/1997 | Kavteladze et al. | |
| 5,690,674 A | 11/1997 | Diaz | |
| 5,693,085 A | 12/1997 | Buirge et al. | |
| 5,702,421 A | 12/1997 | Schneidt | |
| 5,709,707 A | 1/1998 | Lock et al. | |
| 5,713,864 A | 2/1998 | Verkaart | |
| 5,717,259 A | 2/1998 | Schexnayder | |
| 5,720,754 A | 2/1998 | Middleman et al. | |
| 5,725,552 A | 3/1998 | Kotula et al. | |
| 5,733,294 A | 3/1998 | Forber et al. | |
| 5,733,337 A | 3/1998 | Carr, Jr. et al. | |
| 5,741,297 A | 4/1998 | Simon | |
| 5,772,641 A | 6/1998 | Wilson | |
| 5,776,162 A | 7/1998 | Kleshinski | |
| 5,776,183 A | 7/1998 | Kanesaka et al. | |
| 5,797,960 A | 8/1998 | Stevens et al. | |
| 5,800,516 A | 9/1998 | Fine et al. | |
| 5,810,884 A | 9/1998 | Kim | |
| 5,820,594 A | 10/1998 | Fontirroche et al. | |
| 5,823,956 A | 10/1998 | Roth et al. | |
| 5,829,447 A | 11/1998 | Stevens et al. | |
| 5,853,420 A | 12/1998 | Chevillon et al. | |
| 5,853,422 A | 12/1998 | Huebsch et al. | |
| 5,855,614 A | 1/1999 | Stevens et al. | |
| 5,861,003 A | 1/1999 | Latson et al. | |
| 5,865,791 A | 2/1999 | Whayne et al. | |
| 5,879,366 A | 3/1999 | Shaw et al. | |
| 5,893,856 A | 4/1999 | Jacob et al. | |
| 5,902,287 A | 5/1999 | Martin | |
| 5,902,319 A | 5/1999 | Daley | |
| 5,904,703 A | 5/1999 | Gilson | |
| 5,919,200 A | 7/1999 | Stambaugh et al. | |
| 5,924,424 A | 7/1999 | Stevens et al. | |
| 5,928,250 A | 7/1999 | Koike et al. | |
| 5,944,691 A | 8/1999 | Querns et al. | |
| 5,944,738 A | 8/1999 | Amplatz et al. | |
| 5,955,110 A | 9/1999 | Patel et al. | |
| 5,976,174 A | 11/1999 | Ruiz | |
| 5,980,505 A | 11/1999 | Wilson | |
| 5,989,268 A | 11/1999 | Pugsley, Jr. et al. | |
| 5,993,475 A | 11/1999 | Lin et al. | |
| 5,993,844 A | 11/1999 | Abraham et al. | |
| 5,997,575 A | 12/1999 | Whitson et al. | |
| 6,010,517 A | 1/2000 | Baccaro | |
| 6,019,753 A | 2/2000 | Pagan | |
| 6,024,756 A | 2/2000 | Huebsch et al. | |
| 6,027,519 A | 2/2000 | Stanford | |
| 6,030,007 A | 2/2000 | Bassily et al. | |
| 6,056,760 A | 5/2000 | Koike et al. | |
| 6,071,998 A | 6/2000 | Muller et al. | |
| 6,077,291 A | 6/2000 | Das | |
| 6,077,880 A | 6/2000 | Castillo et al. | |
| 6,079,414 A | 6/2000 | Roth | |
| 6,080,182 A | 6/2000 | Shaw et al. | |
| 6,096,347 A | 8/2000 | Geddes et al. | |
| 6,106,913 A | 8/2000 | Scardino et al. | |
| 6,113,609 A | 9/2000 | Adams | |
| 6,117,159 A | 9/2000 | Huebsch et al. | |
| 6,126,686 A | 10/2000 | Badylak et al. | |
| 6,132,438 A | 10/2000 | Fleischman et al. | |
| 6,143,037 A | 11/2000 | Goldstein et al. | |
| 6,152,144 A | 11/2000 | Lesh et al. | |
| 6,165,183 A | 12/2000 | Kuehn et al. | |
| 6,165,204 A | 12/2000 | Levinson et al. | |
| 6,168,588 B1 | 1/2001 | Wilson | |
| 6,171,329 B1 * | 1/2001 | Shaw et al. | 606/213 |
| 6,174,322 B1 | 1/2001 | Schneidt et al. | |
| 6,174,330 B1 | 1/2001 | Stinson | |
| 6,183,443 B1 | 2/2001 | Kratoska et al. | |
| 6,187,039 B1 | 2/2001 | Hiles et al. | |
| 6,190,353 B1 | 2/2001 | Makower et al. | |
| 6,190,357 B1 | 2/2001 | Ferrari et al. | |
| 6,197,016 B1 | 3/2001 | Fourkas et al. | |
| 6,199,262 B1 | 3/2001 | Martin | |
| 6,206,895 B1 | 3/2001 | Levinson | |
| 6,206,907 B1 | 3/2001 | Marino et al. | |
| 6,214,029 B1 | 4/2001 | Thill et al. | |
| 6,217,590 B1 | 4/2001 | Levinson | |
| 6,221,092 B1 | 4/2001 | Koike et al. | |
| 6,227,139 B1 | 5/2001 | Nguyen et al. | |
| 6,228,097 B1 | 5/2001 | Levinson et al. | |

| | | | | | |
|---|---|---|---|---|---|
| 6,231,561 B1 | 5/2001 | Frazier et al. | 6,867,249 B2 | 3/2005 | Lee et al. |
| 6,245,080 B1 | 6/2001 | Levinson | 6,921,410 B2 | 7/2005 | Porter |
| 6,245,537 B1 | 6/2001 | Williams et al. | 2001/0010481 A1 | 8/2001 | Blanc et al. |
| 6,261,309 B1 | 7/2001 | Urbanski | 2001/0014800 A1 | 8/2001 | Frazier et al. |
| 6,265,333 B1 | 7/2001 | Dzenis et al. | 2001/0025132 A1 | 9/2001 | Alferness et al. |
| 6,270,515 B1 | 8/2001 | Linden et al. | 2001/0034537 A1 | 10/2001 | Shaw et al. |
| 6,277,138 B1 | 8/2001 | Levinson et al. | 2001/0034567 A1 | 10/2001 | Allen et al. |
| 6,277,139 B1 | 8/2001 | Levinson et al. | 2001/0037129 A1 | 11/2001 | Thill |
| 6,287,317 B1 | 9/2001 | Makower et al. | 2001/0039435 A1 | 11/2001 | Roue et al. |
| 6,290,674 B1 | 9/2001 | Roue et al. | 2001/0039436 A1 | 11/2001 | Frazier et al. |
| 6,299,635 B1 | 10/2001 | Frantzen | 2001/0041914 A1 | 11/2001 | Frazier et al. |
| 6,306,150 B1 | 10/2001 | Levinson | 2001/0041915 A1 | 11/2001 | Roue et al. |
| 6,306,424 B1 | 10/2001 | Vyakarnam et al. | 2001/0044639 A1 | 11/2001 | Levinson |
| 6,312,443 B1 | 11/2001 | Stone | 2001/0049492 A1 | 12/2001 | Frazier et al. |
| 6,312,446 B1 | 11/2001 | Huebsch et al. | 2002/0010481 A1* | 1/2002 | Jayaraman ............... 606/151 |
| 6,315,791 B1 | 11/2001 | Gingras et al. | 2002/0019648 A1 | 2/2002 | Akerfeldt et al. |
| 6,316,262 B1 | 11/2001 | Huisman et al. | 2002/0022859 A1 | 2/2002 | Hogendijk |
| 6,319,263 B1 | 11/2001 | Levinson | 2002/0022860 A1 | 2/2002 | Borillo et al. |
| 6,322,548 B1 | 11/2001 | Payne et al. | 2002/0026208 A1 | 2/2002 | Roe et al. |
| 6,328,727 B1 | 12/2001 | Frazier et al. | 2002/0029048 A1 | 3/2002 | Miller |
| 6,334,872 B1 | 1/2002 | Termin et al. | 2002/0032459 A1 | 3/2002 | Horzewski et al. |
| 6,342,064 B1 | 1/2002 | Koike et al. | 2002/0032462 A1 | 3/2002 | Houser et al. |
| 6,344,048 B1 | 2/2002 | Chin et al. | 2002/0034259 A1 | 3/2002 | Tada |
| 6,344,049 B1 | 2/2002 | Levinson et al. | 2002/0035374 A1 | 3/2002 | Borillo et al. |
| 6,346,074 B1 | 2/2002 | Roth | 2002/0043307 A1 | 4/2002 | Ishida et al. |
| 6,348,041 B1 | 2/2002 | Klint et al. | 2002/0049457 A1 | 4/2002 | Kaplan et al. |
| 6,352,552 B1 | 3/2002 | Levinson et al. | 2002/0052572 A1 | 5/2002 | Franco et al. |
| 6,355,052 B1 | 3/2002 | Neuss et al. | 2002/0058989 A1 | 5/2002 | Chen et al. |
| 6,356,782 B1 | 3/2002 | Sirimanne et al. | 2002/0077555 A1 | 6/2002 | Schwartz |
| 6,358,238 B1 | 3/2002 | Sherry | 2002/0095174 A1 | 7/2002 | Tsugita et al. |
| 6,364,853 B1 | 4/2002 | French et al. | 2002/0096183 A1 | 7/2002 | Stevens et al. |
| 6,371,904 B1 | 4/2002 | Sirimanne et al. | 2002/0099389 A1 | 7/2002 | Michler et al. |
| 6,375,625 B1 | 4/2002 | French et al. | 2002/0099390 A1 | 7/2002 | Kaplan et al. |
| 6,375,671 B1 | 4/2002 | Kobayashi et al. | 2002/0099437 A1* | 7/2002 | Anson et al. ............... 623/1.15 |
| 6,379,342 B1 | 4/2002 | Levinson | 2002/0103492 A1 | 8/2002 | Kaplan et al. |
| 6,379,368 B1 | 4/2002 | Corcoran et al. | 2002/0107531 A1 | 8/2002 | Schreck et al. |
| 6,387,104 B1 | 5/2002 | Pugsley, Jr. et al. | 2002/0111537 A1 | 8/2002 | Taylor et al. |
| 6,398,796 B2 | 6/2002 | Levinson | 2002/0111637 A1 | 8/2002 | Kaplan et al. |
| 6,402,772 B1 | 6/2002 | Amplatz et al. | 2002/0111647 A1 | 8/2002 | Khairkhahan et al. |
| 6,419,669 B1 | 7/2002 | Frazier et al. | 2002/0120323 A1 | 8/2002 | Thompson et al. |
| 6,426,145 B1 | 7/2002 | Moroni | 2002/0128680 A1 | 9/2002 | Pavlovic |
| 6,436,088 B2 | 8/2002 | Frazier et al. | 2002/0129819 A1 | 9/2002 | Feldman et al. |
| 6,440,152 B1 | 8/2002 | Gainor et al. | 2002/0164729 A1 | 11/2002 | Skraly et al. |
| 6,450,987 B1 | 9/2002 | Kramer | 2002/0169377 A1 | 11/2002 | Khairkhahan et al. |
| 6,460,749 B1 | 10/2002 | Levinson et al. | 2002/0183786 A1 | 12/2002 | Girton |
| 6,482,224 B1 | 11/2002 | Michler et al. | 2002/0183787 A1 | 12/2002 | Wahr et al. |
| 6,488,706 B1 | 12/2002 | Solymar et al. | 2002/0183823 A1 | 12/2002 | Pappu |
| 6,494,846 B1 | 12/2002 | Margolis | 2002/0198563 A1 | 12/2002 | Gainor et al. |
| 6,494,888 B1 | 12/2002 | Laufer et al. | 2003/0004533 A1 | 1/2003 | Dieck et al. |
| 6,508,828 B1 | 1/2003 | Akerfeldt et al. | 2003/0023266 A1 | 1/2003 | Borillo et al. |
| 6,514,515 B1 | 2/2003 | Williams | 2003/0028213 A1 | 2/2003 | Thill et al. |
| 6,548,569 B1 | 4/2003 | Williams et al. | 2003/0045893 A1 | 3/2003 | Ginn |
| 6,551,303 B1 | 4/2003 | Van Tassel et al. | 2003/0050665 A1 | 3/2003 | Ginn |
| 6,551,344 B2 | 4/2003 | Thill | 2003/0055455 A1 | 3/2003 | Yang et al. |
| 6,585,719 B2 | 7/2003 | Wang | 2003/0057156 A1 | 3/2003 | Peterson et al. |
| 6,585,755 B2 | 7/2003 | Jackson et al. | 2003/0059640 A1 | 3/2003 | Marton et al. |
| 6,596,013 B2 | 7/2003 | Yang et al. | 2003/0065379 A1 | 4/2003 | Babbas et al. |
| 6,599,448 B1 | 7/2003 | Ehrhard, Jr. et al. | 2003/0100920 A1 | 5/2003 | Akin et al. |
| 6,610,764 B1 | 8/2003 | Martin et al. | 2003/0120337 A1 | 6/2003 | Van Tassel et al. |
| 6,623,508 B2 | 9/2003 | Shaw et al. | 2003/0139819 A1 | 7/2003 | Beer et al. |
| 6,623,518 B2 | 9/2003 | Thompson et al. | 2003/0171774 A1 | 9/2003 | Freudenthal et al. |
| 6,626,936 B2 | 9/2003 | Stinson | 2003/0191495 A1 | 10/2003 | Ryan et al. |
| 6,629,901 B2 | 10/2003 | Huang | 2003/0195530 A1 | 10/2003 | Thill |
| 6,666,861 B1 | 12/2003 | Grabek | 2003/0204203 A1 | 10/2003 | Khairkhahan et al. |
| 6,669,722 B2 | 12/2003 | Chen et al. | 2004/0044361 A1 | 3/2004 | Frazier et al. |
| 6,689,589 B2 | 2/2004 | Huisman et al. | 2004/0073242 A1 | 4/2004 | Chanduszko |
| 6,712,804 B2 | 3/2004 | Roue et al. | 2004/0176799 A1 | 9/2004 | Chanduszko et al. |
| 6,712,836 B1 | 3/2004 | Berg et al. | 2004/0210301 A1 | 10/2004 | Obermiller |
| 6,726,696 B1 | 4/2004 | Houser et al. | 2004/0234567 A1 | 11/2004 | Dawson |
| 6,828,357 B1 | 12/2004 | Martin et al. | 2005/0025809 A1 | 2/2005 | Hasirci et al. |
| 6,838,493 B2 | 1/2005 | Williams et al. | 2005/0043759 A1 | 2/2005 | Chanduszko |
| 6,867,247 B2 | 3/2005 | Williams et al. | 2005/0113868 A1 | 5/2005 | Devellian et al. |
| 6,867,248 B1 | 3/2005 | Martin et al. | 2005/0267523 A1 | 12/2005 | Devellian et al. |

| | | | |
|---|---|---|---|
| 2005/0273135 A1 | 12/2005 | Chanduszko et al. | |
| 2005/0288786 A1 | 12/2005 | Chanduszko | |
| 2006/0122647 A1 | 6/2006 | Callaghan et al. | |
| 2006/0265004 A1 | 11/2006 | Callaghan et al. | |
| 2007/0010851 A1 | 1/2007 | Chanduszko et al. | |
| 2007/0167981 A1 | 7/2007 | Opolski | |

FOREIGN PATENT DOCUMENTS

| | | | |
|---|---|---|---|
| EP | | 0362113 | 4/1990 |
| EP | | 0474887 A1 | 3/1992 |
| EP | | 0 839 549 | 5/1998 |
| EP | | 0839549 A1 | 5/1998 |
| EP | | 0 861 632 | 9/1998 |
| EP | | 1013227 A2 | 6/2000 |
| EP | | 1046375 A1 | 10/2000 |
| EP | | 1222897 A2 | 7/2002 |
| WO | WO-96/25179 A1 | | 8/1996 |
| WO | WO-96/31157 A1 | | 10/1996 |
| WO | WO-98/07375 A1 | | 2/1998 |
| WO | WO 98/08462 | | 3/1998 |
| WO | WO 98/16174 | | 4/1998 |
| WO | WO-98/29026 | | 7/1998 |
| WO | WO-98/51812 | | 11/1998 |
| WO | WO-99/05977 A1 | | 2/1999 |
| WO | WO-98/18864 | | 4/1999 |
| WO | WO-99/18862 A1 | | 4/1999 |
| WO | WO-99/18864 | | 4/1999 |
| WO | WO-99/18870 A1 | | 4/1999 |
| WO | WO-99/18871 A1 | | 4/1999 |
| WO | WO-99/30640 A1 | | 6/1999 |
| WO | WO-00/27292 A1 | | 5/2000 |
| WO | WO-00/44428 A2 | | 8/2000 |
| WO | WO-01/08600 | | 2/2001 |
| WO | WO-01/19256 | | 3/2001 |
| WO | WO-01/21247 A1 | | 3/2001 |
| WO | WO-01/28432 | | 4/2001 |
| WO | WO-01/30268 A1 | | 5/2001 |
| WO | WO-01/49185 A1 | | 7/2001 |
| WO | WO-01/78596 A1 | | 10/2001 |
| WO | WO-01/93783 | | 12/2001 |
| WO | WO-02/17809 A1 | | 3/2002 |
| WO | WO-02/24106 A3 | | 3/2002 |
| WO | WO-03/024337 | | 3/2003 |
| WO | WO-03/053493 A1 | | 7/2003 |
| WO | WO-03/53493 A2 | | 7/2003 |
| WO | WO-03/059152 | | 7/2003 |
| WO | WO-03/063732 A | | 8/2003 |
| WO | WO-03/077733 A2 | | 9/2003 |
| WO | WO-03/082076 | | 10/2003 |
| WO | WO-03/103476 | | 12/2003 |
| WO | WO-2004/032993 | | 4/2004 |
| WO | WO-2004/037333 | | 5/2004 |
| WO | WO-2004/043266 | | 5/2004 |
| WO | WO-2004/043508 | | 5/2004 |
| WO | WO-2004/052213 | | 6/2004 |
| WO | WO-2005/006990 | | 1/2005 |
| WO | WO-2005/018728 | | 3/2005 |
| WO | WO-2005/027752 | | 3/2005 |
| WO | WO-2005/074813 | | 8/2005 |
| WO | WO-2005/092203 | | 10/2005 |
| WO | WO-2005/110240 | | 11/2005 |
| WO | WO-2005/112779 | | 12/2005 |
| WO | WO-2006/036837 | | 4/2006 |
| WO | WO-2006/102213 | | 9/2006 |

OTHER PUBLICATIONS

Athanasion, T., "Coronary Artery Bypass with the Use of a Magnetic Distal Anastomotic Device: Surgical Technique and Preliminary Experience," The Heart Surgery Forum #2004-1024, 2004, 4 pgs.

Bachthaler, M. et al., "Corrosion of Tungsten Coils After Peripheral Vascular Embolization Theraphy: Influence on Outcome and Tungsten Load", *Catherization and Cardiovascular Interventions*, vol. 62, pp. 380-384, 2004.

Barroso, L.A. et al., "RPM: A Rapid Prototyping Engine for Multiprocessor Systems", IEEE Computer, Feb. 1995, pp. 26-34.

Berg SLT/MST Connector System, Berg Electronics, Du Pont Bulletin, 1260, Oct. 1983.

Boxer, A. "Where Buses Cannot Go", IEEE Spectrum, Feb. 1995, pp. 41-45.

Connector System for Transmission-Line Cables, Wilding, Eleventh Annual Connector Symposium Proceedings, pp. 308-316, Oct. 1978.

Definition of "adverse", 1996, Microsoft Bookshelf Basics, The American Heritage Dictionary of the English Language, 3.sup.rd edition, Haughton Mifflin Co., INSO Corp.

European Examination Report, European Application No. 03779297.5, mailed Mar. 15, 2007 (6 pgs.).

European Examination Report, European Application No. 04781644.2, mailed Aug. 23, 2007 (3 pgs).

European Search Report, European Application No. 03729663.9, mailed Feb. 20, 2008 (3 pgs).

Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.

Filsoufi, F., et al., "Automated Distal Coronary Bypass with a Novel Magnetic Coupler (MVP system)," J. Thoracic and Cardiovascular Surgery, vol. 127(1), pp. 185-192.

Huang, X., et al. Passive Mode-Locking in 1.3 μm Two-Section InAs Quantum Dot Lasers, Applied Physics Letters, 2001, vol. 78(19) pp. 2825-2828.

Huang, Y., et al "Logic Gates and Computation from Assembled Nanowire Building Blocks," *Science*, Nov. 9, 2001, vol. 294, pp. 1313-1316.

Imholt, T. J., "Nanotubes in Microwave Fields: Light Emission, Intense Heat, Outgassing, and Reconstructin," Downloaded from Web, 2004, pp. 1-2.

International Search Report for International Patent Application No. PCT/AU03/00759, filed Jun. 19, 2003.

International Search Report, International Application No. PCT/US02/40850 mailed Jun. 19, 2003 (4 pgs).

International Search Report, International Application No. PCT/US03/01050, mailed Jul. 8, 2003 (1 pg).

International Search Report, International Application No. PCT/US03/09051, mailed Sep. 29, 2003 (2 pgs).

International Search Report, International Application No. PCT/US03/17390 mailed Oct. 6, 2003 (4 pgs).

International Search Report, International Application No. PCT/US03/17715, mailed Mar. 24, 2004 (2 pgs).

International Search Report, International Application No. PCT/US03/32133, mailed Apr. 22, 2004 (1 pg).

International Search Report, International Application No. PCT/US03/34003 mailed Oct. 3, 2004 (4 pgs).

International Search Report, International Application No. PCT/US03/35479, mailed Apr. 14, 2004 (2 pgs).

International Search Report, International Application No. PCT/US03/35998 mailed Jun. 16, 2004 (5 pgs).

International Search Report, International Application No. PCT/US03/39253, mailed Apr. 19, 2004 (4 pgs).

International Search Report, International Application No. PCT/US04/022643, mailed Mar. 31, 2005 (2 pgs).

International Search Report, International Application No. PCT/US04/026998, mailed Apr. 22, 2005 (5 pgs).

International Search Report, International Application No. PCT/US04/029978, mailed Jan. 26, 2005 (3 pgs).

International Search Report, International Application No. PCT/US05/006703, mailed Jul. 25, 2005 (3 pgs).

International Search Report, International Application No. PCT/US05/013705 mailed Aug. 4, 2005 (4 pgs).

International Search Report, International Application No. PCT/US05/015382, mailed Oct. 6, 2005 (4 pgs).

International Search Report, International Application No. PCT/US05/34276, mailed 9 Oct. 2007.

International Search Report, International Application No. PCT/US06/009978, mailed Jul. 13, 2006 (2 pgs).
International Search Report, International Application No. PCT/US07/065546, mailed 29 Oct. 2007 (4 pgs).
International Search Report, International Application No. PCT/US2007/065541, mailed Aug. 7, 2007 (4 pgs).
International Search Report, International Application No. PCT/US97/14822, mailed Feb. 20, 1998 (2 pgs).
International Search Report, International Application No. PCT/US97/17927, mailed Feb. 10, 1998 (1 pg).
Islam, M. F. et al. "High Weight Fraction Surfactant Solubilization of Single-Wall Carbon Nanotubes in Water," *Nano Letters*, Jan. 16, 2003, vol. 3, No. 2, pp. 269-273.
Isotalo, T. et al., "Biocompatibility Testing of a New Bioabsorbable X-Ray Positive SR-PLA 96/4 Urethral Stent", *The Journal of Urology*, vol. 163, pp. 1764-1767, Nov. 1999.
Javey, A., et al., "Carbon Nanotube Transistor Arrays for Multistage Complementary Logic and Ring Oscillators," *Nano Letters*, 2002, vol. 2, No. 9, pp. 929-932.
Kimura, A., et al., "Effects of Neutron Irradiation on the Transformation Behavior in Ti-Ni Alloys," Abstract, Proceedings of the Int'l Conf. On Mariensitic Transformations, 1992, pp. 935-940.
Klima, U., "Magnetic Vascular Port in Minimally Invasive Direct Coronary Artery Bypass Grafting," Circulation, 2004, 11-55 -11-60.
Meier, MD, Bernhard et al., "Contemporary Management of Patent Foramen Ovale," American Heart Association, Inc., Circulation, 2003, vol. 107, pp. 5-9.
Nat'l Aeronautics and Space Administration, "55-Nitinol—The Alloy iwth a Memory: Its Physical Metallurgy, Properties, ans Applications," NASA Report, pp. 24-25.
Ogawa et al., Fiber Diffraction Methods, 47, pp. 353-362 (1980).
Parviainen, M. et al., "A New Biodegradable Stent for the Pancreaticojejunal Anastomosis After Pancreaticoduodenal Resection: In Vitro Examination and Pilot Experiences in Humans", *Pancreas*, vol. 21, No. 1, pp. 14-21, 2000.
Ramanathan, G., et al., "Experimental and Computational Methods for Shape Memory Alloys," 15th ASCE Engineering Mechanics Conference, Jun. 2-5, 2002.
Ruddy, a.C. et al., "Rheological, Mechanical and Thermal Behaviour of Radipaque Filled Polymers", *Polymer Processing Research Centre, School of Chemical Engineering, Queen's University of Belfast*, 5 pgs.
Ruiz, et al, "The Puncture Technique: A New Method for Transcatheter Closure of Patent Foramen Ovale," Catheterization and Cardiovascular Interventions, 2001, vol. 53, pp. 369-372.
Shabalovskaya, S., "Surface, Corrosion and Biocompatibility Aspects of Nitinol as an Implant Material," Bio-Medical Materials and Engineering, 2002, vol. 12, pp. 69-109.
Simpson et al., Microbiology, vol. 141, pp. 1451-1460 (1995).
SMST-2000, "Proceedings of the International Conference on Shape Memory and Superelastic Technologies," 30 Apr. To May 4, 2000, Asilomar Conference Center.
Stein, H., "Telemanipulator-gestüutzte Applikation eines magnetischen Gefäβ-Kopplers am schlagenden Herzen mit dem da Vinci™ -Surgical-System," Biomedizinische Technik, 2003, vol. 48(9), pp. 230-234.
Stockel, "Nitinol Medical Devices and Implants," SMST-2000 Conference Proceedings, 2001, pgs. 531-541.
Uchil, J., "Shape Memory Alloys—Characterization Techniques," Pramana—Journal of Physics, 2002, vol. 58(5)(6), pp. 1131-1139.
Vaajanen, A. et al., "Expansion and Fixation Properties of a New Braided Biodegradable Urethral Stent: An Experimental Study in the Rabbit", *The Journal of Urology*, vol. 169, pp. 1771-1174, Mar. 2003.
Virag et al., "Effects of poly (ADP-ribose) polymerase Inhibition on inflammatory cell migration in a murine model of asthma." Med. Sci. Monit, 2004, vol. 10, pp. BR77-83.

* cited by examiner

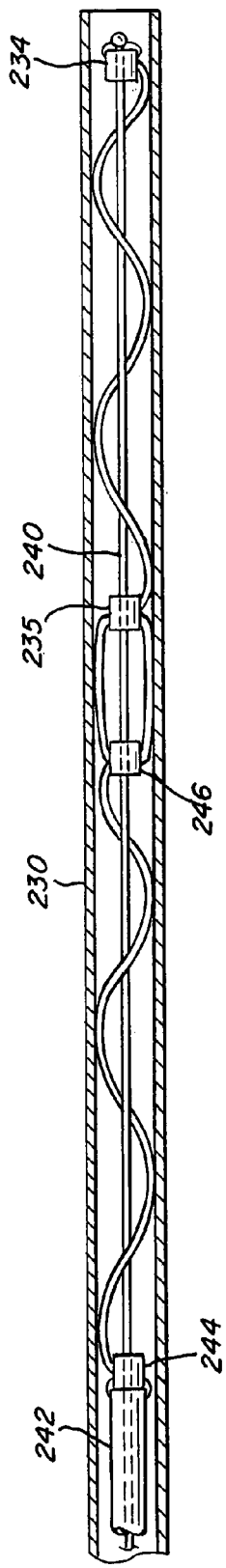
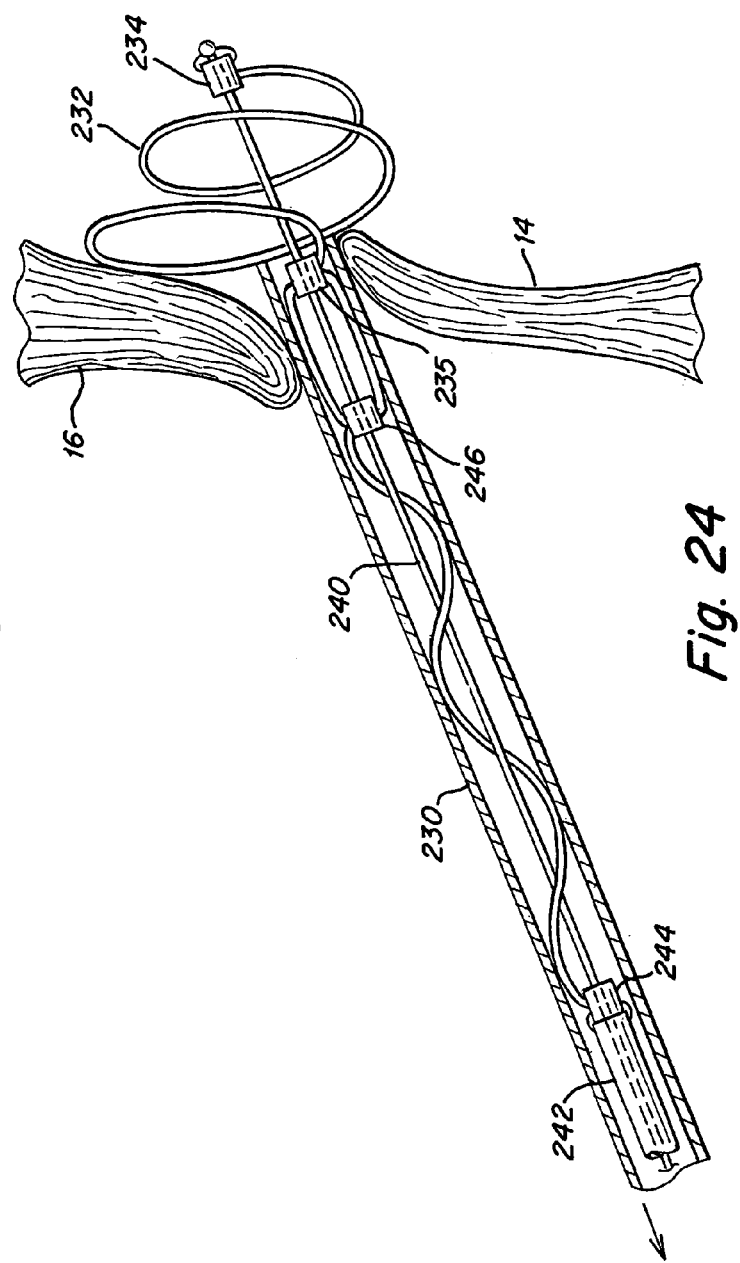
Fig. 23
Fig. 24

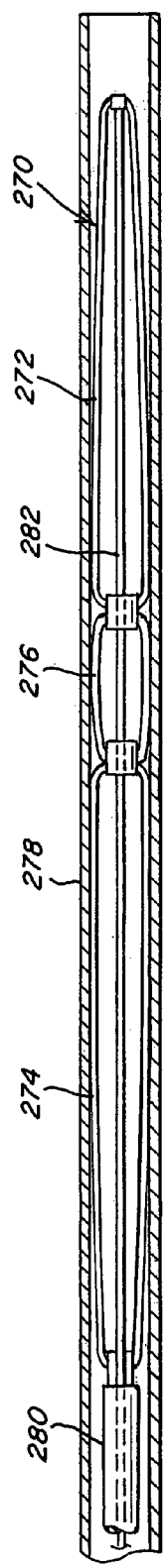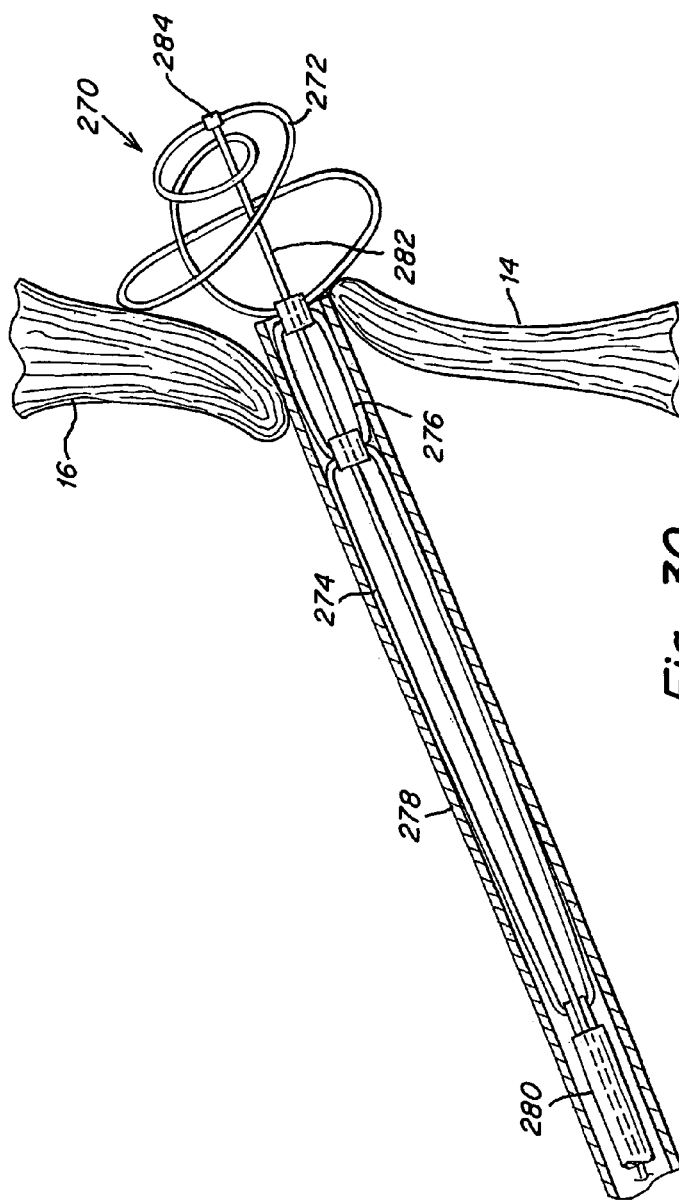
Fig. 29
Fig. 30

DOUBLE COIL OCCLUDER

CROSS-REFERENCE TO RELATED APPLICATION

This application claims priority from provisional Ser. No. 60/568,526, filed May 6, 2004, which is incorporated herein by reference.

BACKGROUND

This invention relates to an occluder for closing a septal defect.

A PFO, illustrated in FIG. 1, is a persistent, one-way, usually flap-like opening in the wall between the right atrium 10 and left atrium 12 of the heart. Because left atrial pressure is normally higher than right atrial pressure, the flap formed by septum primum 14 and septum secundum 16 usually stays closed. Under certain conditions, however, right atrial pressure can exceed left atrial pressure, which creates the possibility that blood could pass from the right atrium to the left atrium through a PFO tunnel 18 and allow blood clots to enter the systemic circulation. It is desirable to avoid this situation.

SUMMARY

Embodiments of the present invention relate to an occluder that has a coil on one or both sides of a medical defect, particularly a septal defect such as a patent foramen ovale (PFO). Each coil is preferably provided as a tube that is hollow, with or without a closed end. In some embodiments, the tube can be delivered over a wire.

In the case of use for occluding a PFO, the coils can be designed to provide a compressive force to one or both of septum primum and septum secundum of a PFO. The device can further include a tissue scaffold.

Other features and advantages will become apparent from the following detailed description and drawings.

DESCRIPTION OF THE DRAWINGS

FIGS. 23-26 are partial cross-sectional, partial side views of a device of the type shown in FIG. 22 being delivered to a PFO.

FIGS. 29-32 are partial side, partial cross-sectional views showing the delivery of the device of the type shown in FIGS. 27 and 28.

DETAILED DESCRIPTION

Figure 1:
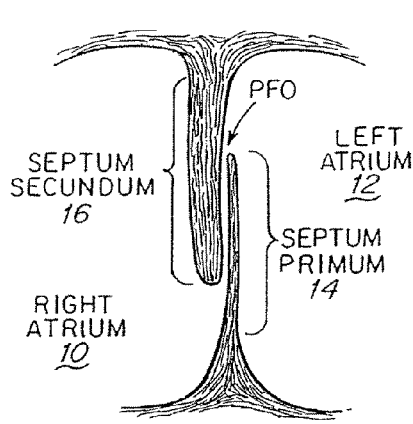
FIG. 1 is a cross-sectional view showing a patent foramen ovale (PFO).

The present invention relates to embodiments of a septal occluder with one or two spiral coils, including a double spiral coil embodiment. The coils are preferably hollow with open or closed ends, and either or both are designed to provide a compressive force when deployed in a septal defect, such as a PFO. While the coils are preferably formed from hollow tubes that can increase the strength of the spirals over solid wires, solid wires could be used. The hollow tubes may also be easier to deliver, and can be provided over a wire. Another double spiral coil design is shown in provisional application Ser. No. 60/528,022, filed Dec. 9, 2003, and in the nonprovisional Ser. No. 11/008,539, filed Dec. 9, 2004, each of which is expressly incorporated by reference.

Referring to FIGS. 2A-4, in this embodiment, an occluder 20 has two coils, a proximal (right atrial) coil 22 and a distal (left atrial) coil 24. These coils are coupled together through a center joint 26. This center joint has a first collar 28 at an inner end of coil 22, a second collar 30 at an inner end of coil 24, and connecting rods 32 and 34 coupling collars 28 and 30. As indicated in FIGS. 2B and 3A, rods 32 and 34 are preferably in a horizontal plane in a position shown in FIG. 4 in a manufactured and non-deployed position.

Figure 3A:
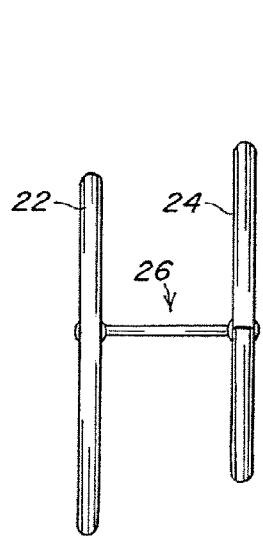
Figure 3B:
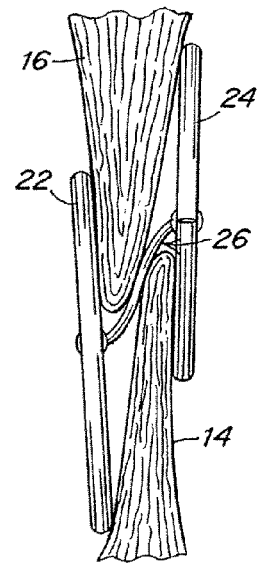
Figure 4:
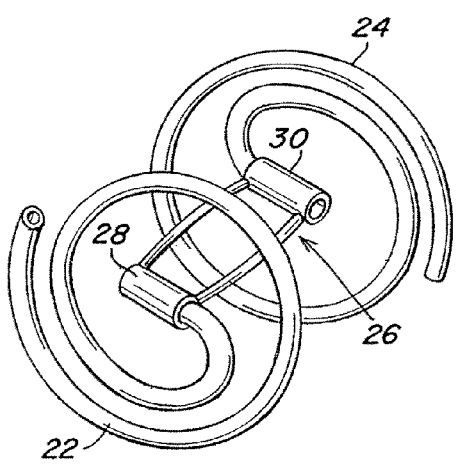

Referring to FIG. 3B, when occluder 20 is in the deployed position in a PFO, coils 22 and 24 each have an upper portion in contact with septum secundum 16 and a lower portion in contact with septum primum 14. As is also indicated, rods 32 and 34 and center joint 26 can extend side-by-side in, and conform to, the geometry of the PFO tunnel between septum primum 14 and septum secundum 16.

The coils can be made from a number of different materials, including metal or nonmetal. Among nonmetals, a preferable material is a polymer, which can be a bioresorbable polymer. In this embodiment, the ends of the coils are shown as being open, but one or both of the ends could be closed, either with a solid piece or with a mesh. In this embodiment, the coils spiral outwardly from a central location.

Figure 5:
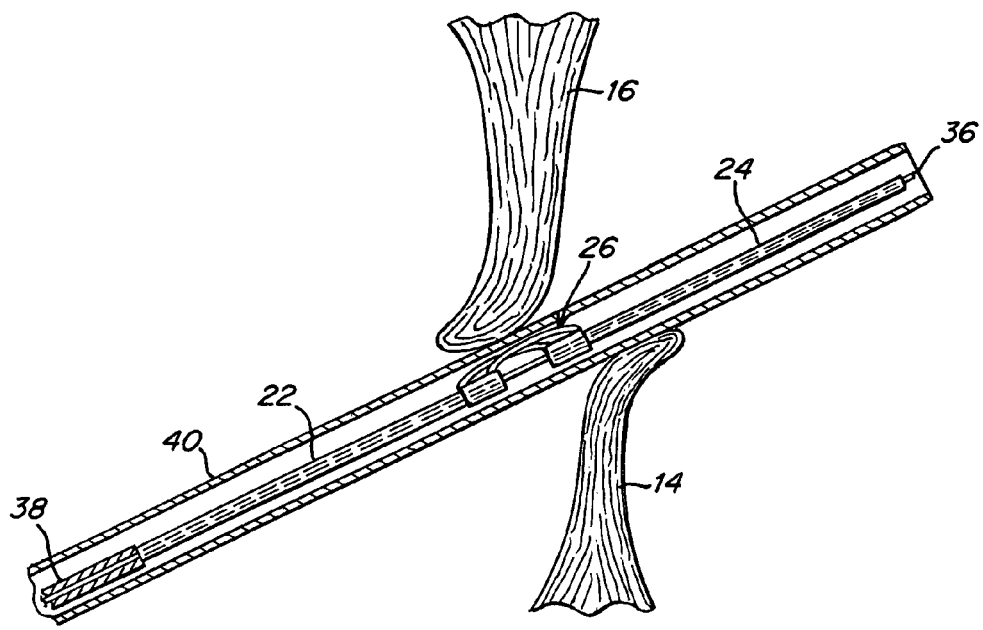
FIGS. 5-8 are partial side and partial cross-sectional views showing delivery of the device of the type shown in FIG. 4.

As shown in FIG. 5, the device with coils in the form of hollow tubes can be mounted over a wire 36 that extends through an inner catheter 38. Wire 36 and catheter 38 are both in a delivery sheath 40. The device with coil 24, coil 22, and center joint 26 is in a substantially elongated and a low profile configuration, such that they fit into a sheath that is preferably 10 French or smaller, although a larger sheath could be used.

Figure 6:
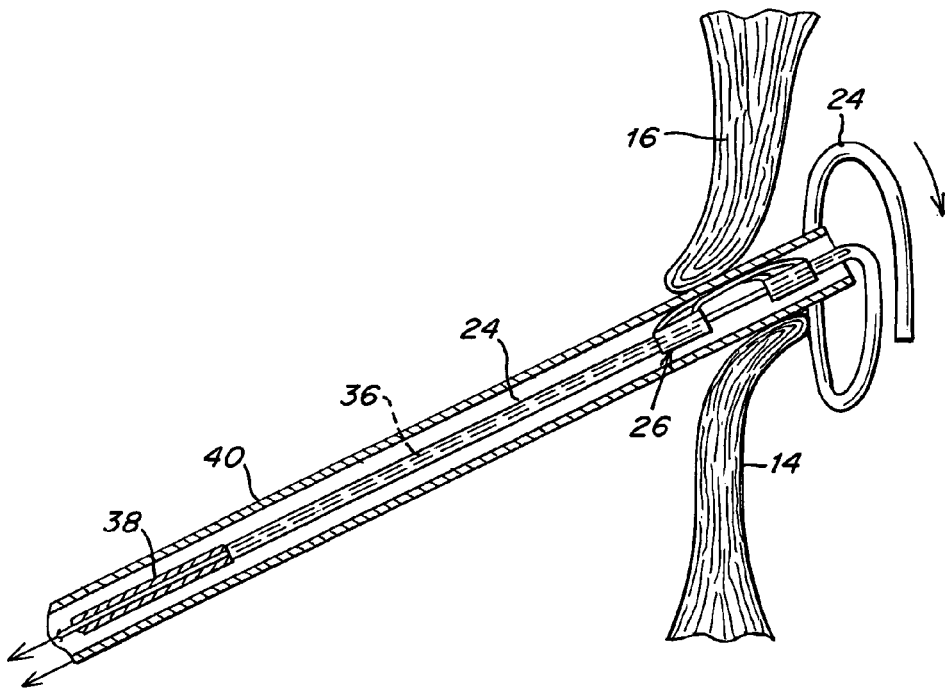

As shown in FIG. 5, sheath 40 is inserted into the left atrium. Referring to FIG. 6, sheath 40 and wire 36 are retracted, while inner catheter 38 is maintained in its current position to hold the position of coil 24. These relative movements, which can be at the same or at different rates, allow coil 24 to be released from delivery sheath 40 and into the left atrium. The coil is preferably formed from a material with good shape memory properties so that it returns to its coil form when released from sheath 40. Such a material is especially useful when the coil has a free outer end not connected to anything else.

Figure 7:
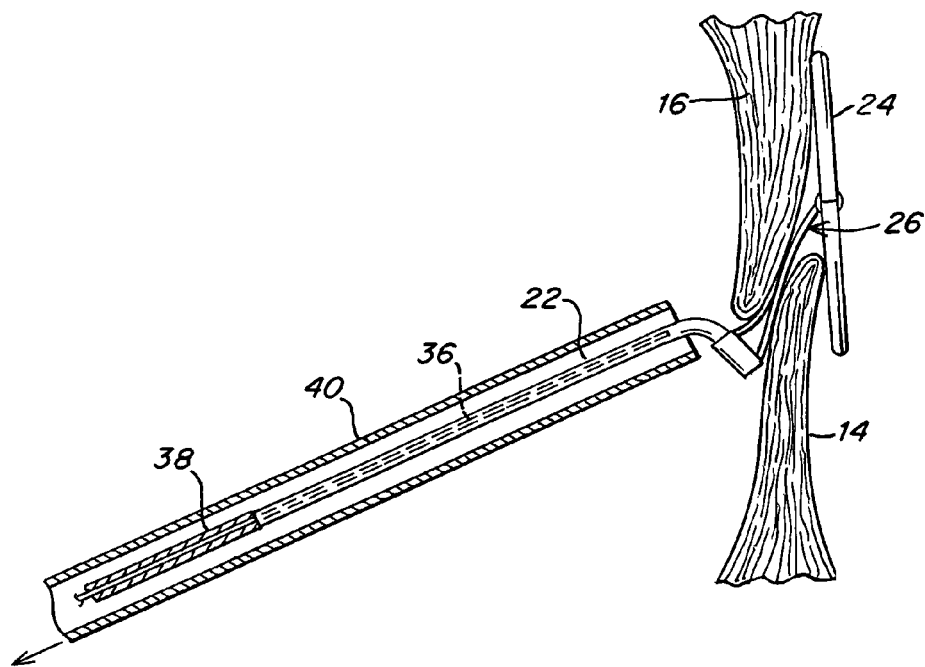
Figure 8:
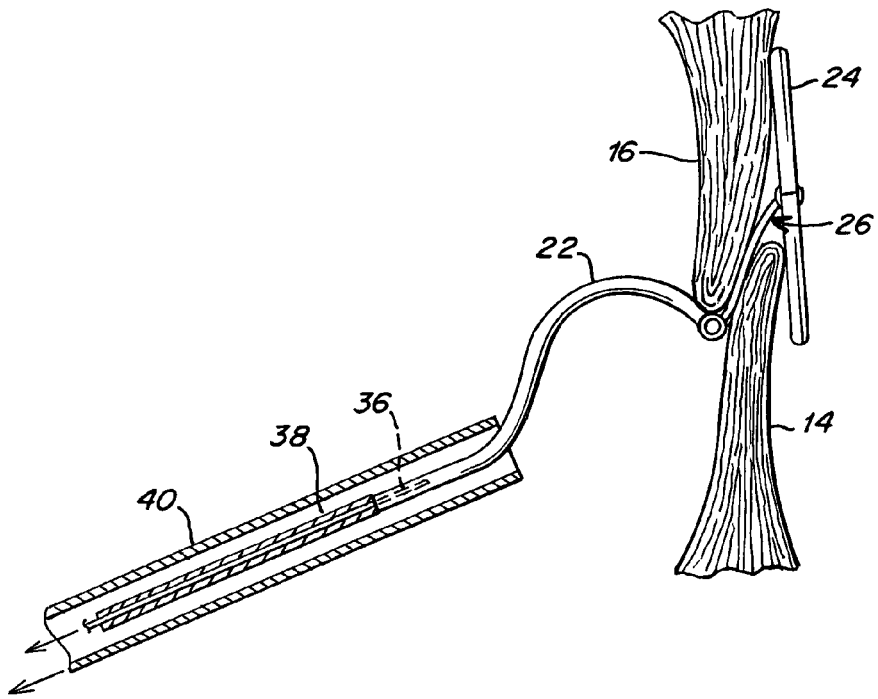

Referring to FIGS. 7 and 8, sheath 40 and wire 36 are retracted further while inner catheter 38 is used to help maintain conduit 22 in a desired position. With such further removal, the center joint is positioned within the PFO tunnel, and coil 22 is allowed to resume its coil shape on the right atrial side of the PFO.

The device is formed with suitable materials, dimensions, and configuration so that the coils provide enough compressive force to hold together septum primum and septum secundum sufficiently to prevent clots from passing from the right atrial side to the left atrial side. As will be apparent below, while occluder 20 has a spiral that is connected to a center joint and spirals outwardly (i.e., with an increasing radius) to a free end, in other embodiments, the coil spirals inwardly from the center joint and may have an end that is connected to the center joint. In this embodiment and others, the outer surface can be roughened to produce an inflammatory effect to encourage healing. In this embodiment and others, a single coil can be used on one side of the defect, with another structure, such as an umbrella-shaped structure on the other side of the defect.

Figure 9:
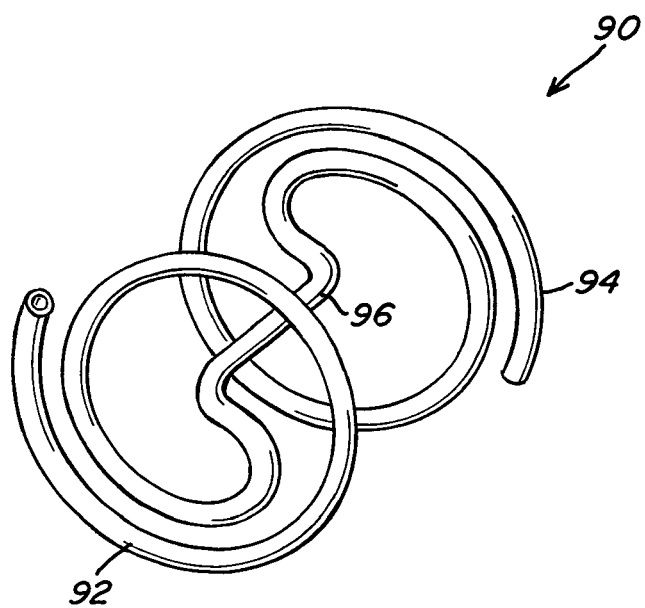
FIGS. 9 and 10 are perspective views of additional embodiments of a device according to the present invention.

FIG. 9 is a perspective view of another embodiment of the present invention in which a device 90 is formed from a single, monolithic hollow tube shaped to form a distal coil 94, a proximal coil 92, and a connecting segment 96 that extends from the inner ends of coils 92 and 94. If desired, portions of device 90, such as at connecting segment 96, can have whiskers that can be formed by gluing short threads of the material used to make the tube or some other material, or connecting segment 96 can be partially shaved or otherwise frayed. The use of whiskers can serve as an inflammatory agent that encourages healing. While mentioned here, whiskers could be used in other embodiments.

Figure 2A:
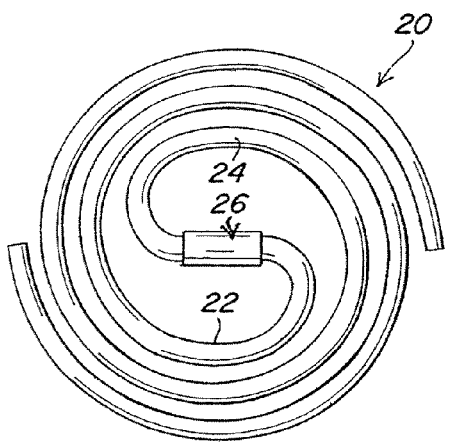
FIGS. 2A, 2B, 3A, 3B, and 4 are various side, end, and perspective views of a device according to a first embodiment of the present invention.
Figure 2B:
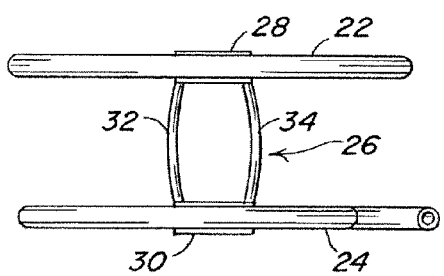

Like the embodiment of FIG. 2a, the inner ends (i.e., smaller radius portion) of the coils are coupled to a connector or transition to a connecting segment, and the outer ends of the coils are free and are not connected to any other structure.

Figure 10:
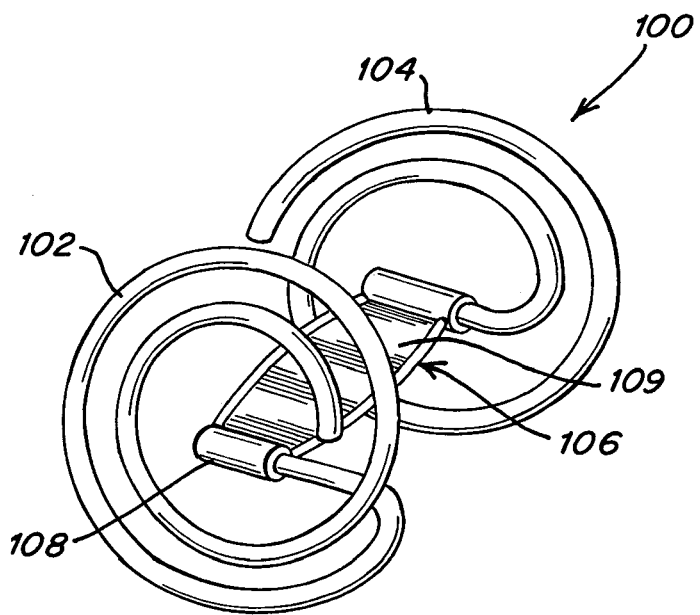

Referring to FIG. 10, in another embodiment of the present invention, a device 100 has a proximal coil 102 and distal coil 104. In this case, one of the coils, in this case coil 102, starts spiraling from the inside where there is a free end, and spirals out with increasing radius to an outer end of coil 102 where the coil is then curved away from the plane of the spiral and is connected to a collar 108 of a center joint 106. Distal coil 104 is shaped in a similar manner.

As is further indicated in FIG. 10, a tissue scaffold 109 can be incorporated into center joint 106. The scaffold is connected between the collars and can be bounded by the connecting rods between the collars, although it could be used at other locations instead of this location or additionally at other locations. While shown between the connecting rods, it can extend around the connecting rods and/or around other portions of the device to encapsulate them. The tissue scaffold promotes encapsulation and endothelialization, thereby further encouraging anatomical closure of septum primum and septum secundum. While shown just in FIG. 10, a tissue scaffold can be incorporated into other embodiments.

A tissue scaffold can be formed of any flexible, biocompatible material capable of promoting tissue growth, including but not limited to polyester fabrics, Teflon-based materials, such as ePTFE, polyurethanes, metallic materials, polyvinyl alcohol (PVA), extracellular matrix (ECM) or other bioengineered materials, synthetic bioresorbable polymeric scaffolds, other natural materials (e.g. collagen), or combinations of these materials. A tissue scaffold or the spiral or center joint can have drugs or biological agents to improve the defect healing process and/or to prevent clotting.

Figure 11:
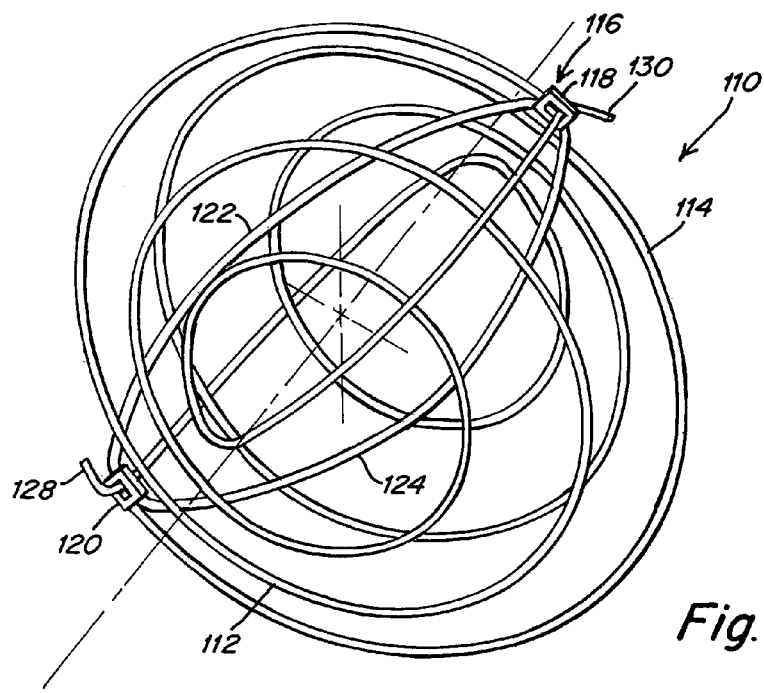
FIGS. 11-16 are perspective, plan, end, and side views of an occluder according to another embodiment of the present invention.
Figure 12:
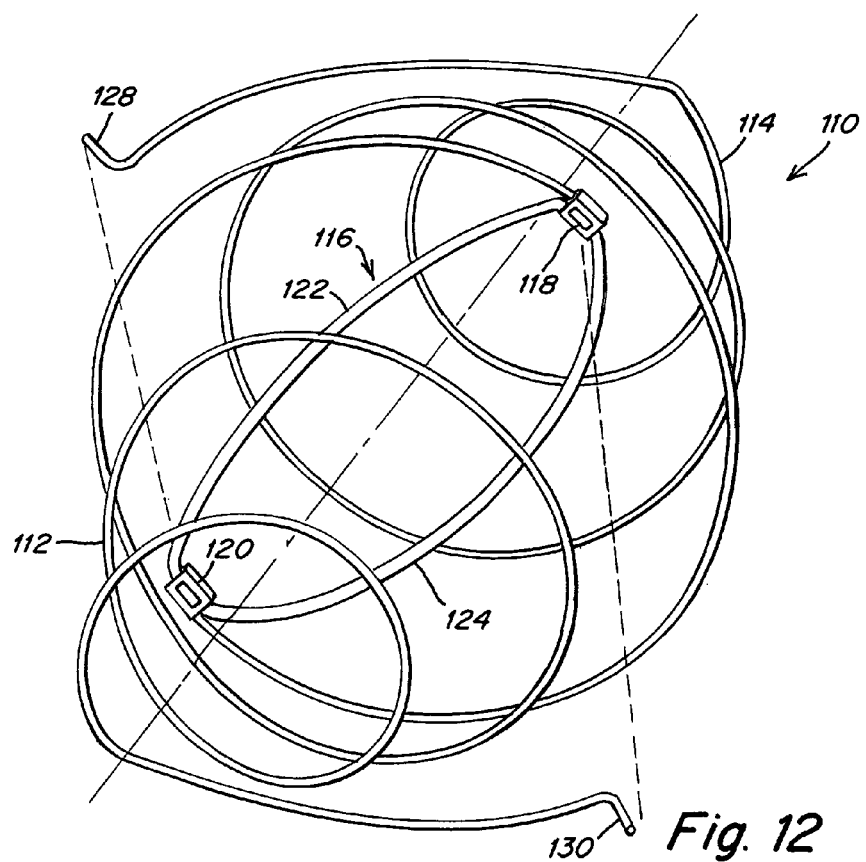

Referring to FIGS. 11-16, a device 110 according to still another embodiment can have close-ended hollow or solid spirals, and can have a free end of a coil on one or both sides of a defect locked to a center joint (FIG. 11) or unlocked (FIG. 12). By locking one or both free ends of a spiral to a center joint, the clamping force of the device can be increased relative to a device with a free end.

A center joint 116 has a latching loop 120 connected to an outer end of coil 114. From the inner end of coil 114, there is a free end 128 that can extend a short distance through loop 120. Similarly, coil 112 has an outer end attached to a latching loop 118 and an inner end that extends to a free end 130 that extends a short distance through the opening in loop 118. Free ends 128 and 130 each have a bent end that extends through latching loops 118 and 120 in a manner that they stay in the latched position. Latching loops 118 and 120 are connected together with connecting rods 122 and 124.

Figure 13:
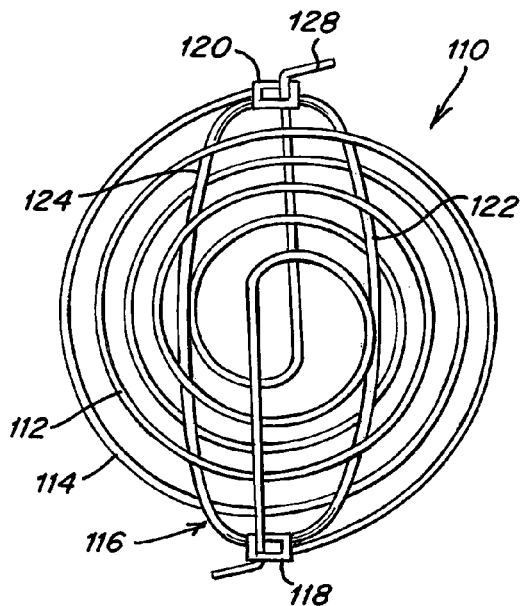
Figure 14:
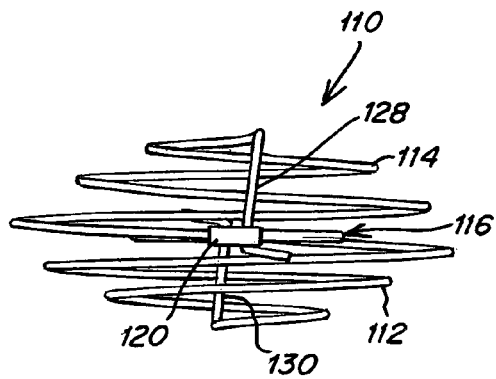
Figure 15:
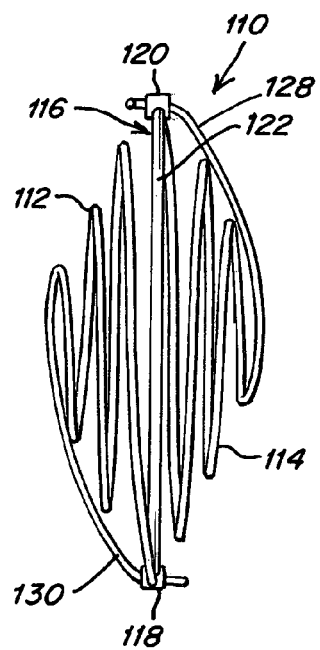
Figure 16:
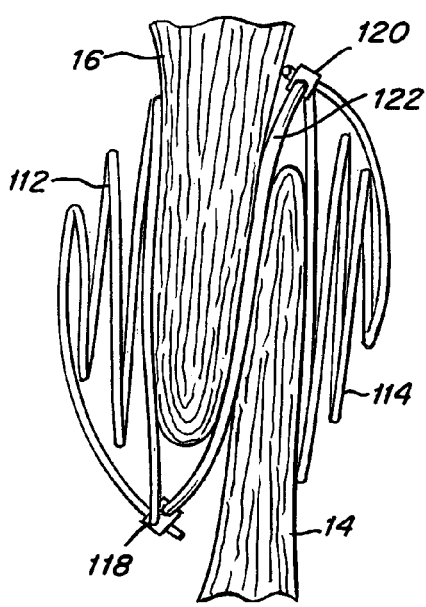

Additional views of this device are shown in FIGS. 13-15 and in FIG. 16 which shows the device as deployed. FIG. 15, in particular, shows how the latching loops 118 and 120 are coupled to the outer ends of the spiral, the spirals extend inwardly, and at the inner end of the spiral, a free end 128, 130 extends to the latching loop on each side. As is also shown in FIG. 16, the connecting rods 122 and 124 (not shown) have some ability to bend and conform to the geometry of the PFO tunnel, while the spirals can provide a compressive force between septum primum and septum secundum.

Figure 17:
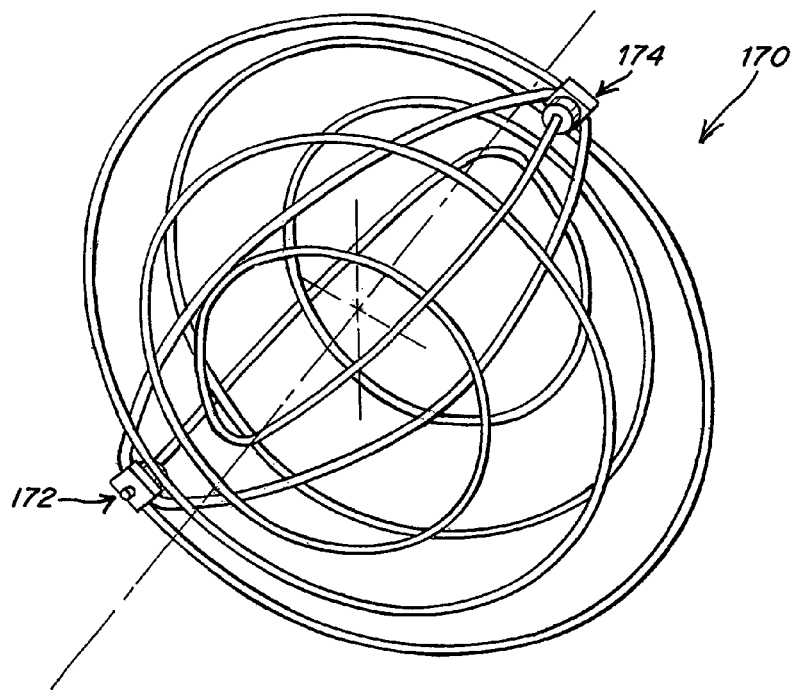
FIGS. 17 and 18 are perspective views of another embodiment of the present invention, which is a variation of the embodiment of FIG. 11.
Figure 18:
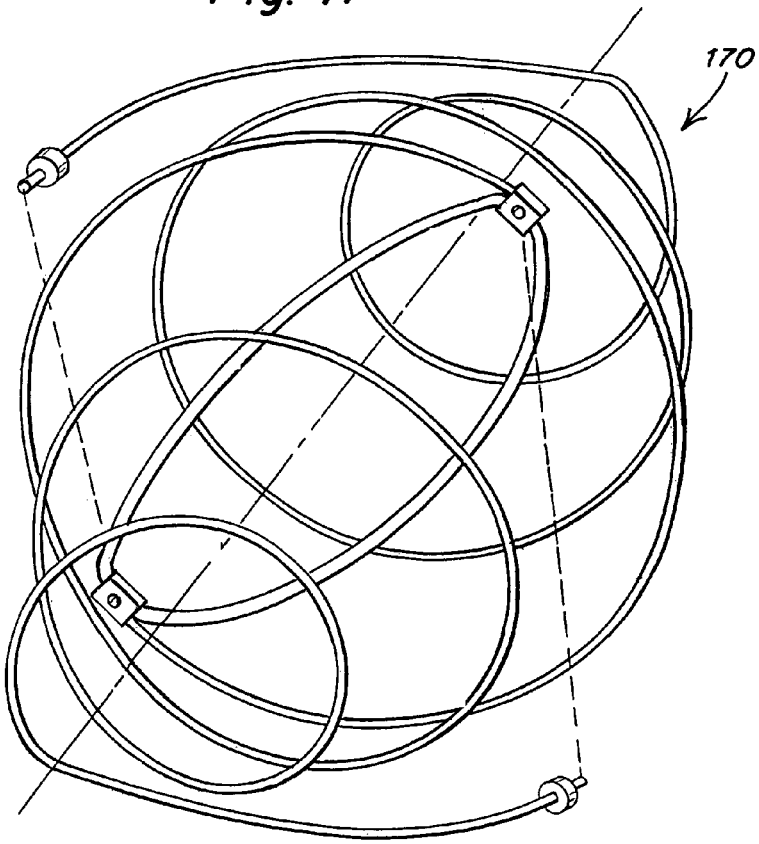

FIGS. 17 and 18 show an embodiment of a device 170 that is similar to that in FIGS. 11 and 12, except that rather than having free ends extending a short way through loops and held in the loops with bent ends, it has locks, such as magnetic locks, 172, 174 on the free ends. In this case, the free end has one magnetic piece and the center joint has another magnet and a conforming mechanical structure, such as a short lug and an opening for receiving the lug.

Figure 19:
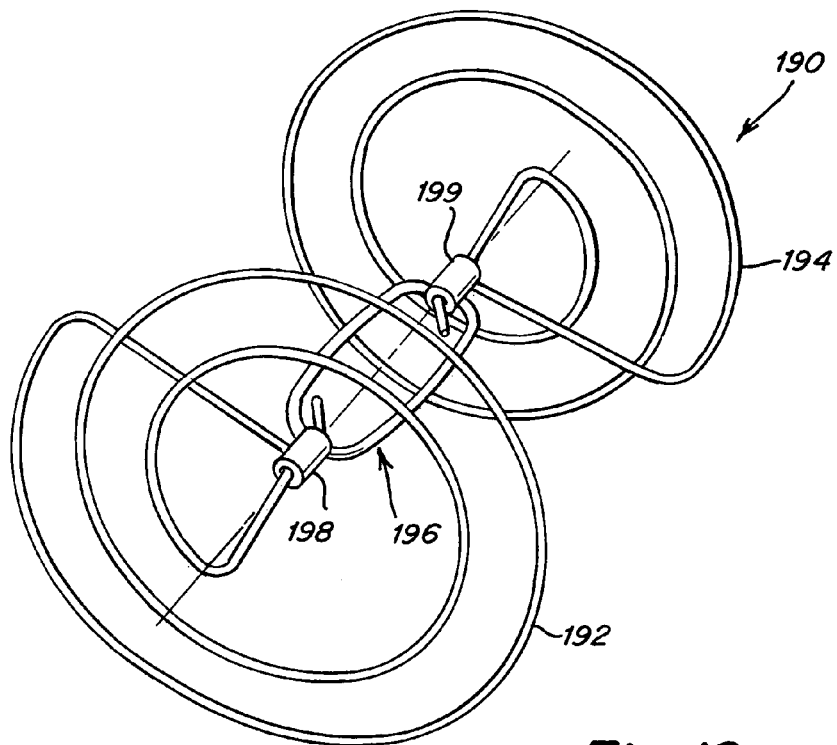
FIGS. 19 and 20, and FIGS. 21 and 22 are perspective views of two additional embodiments of the present invention.
Figure 20:
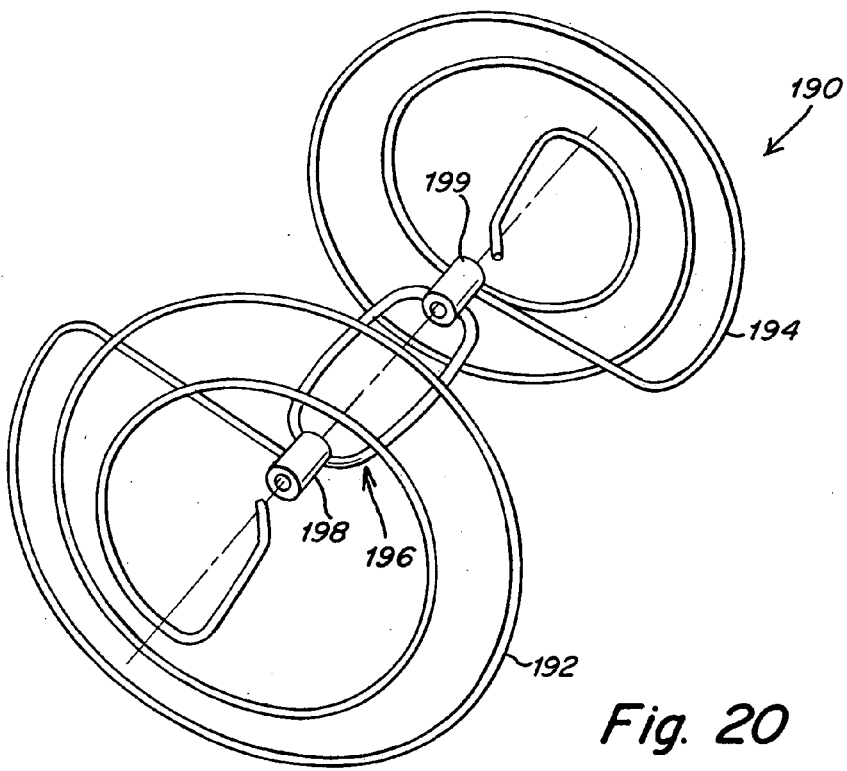

Referring to FIGS. 19 and 20, a device 190 has features of several of the embodiments above. The device has a proximal coil 192 and a distal coil 194 connected together through a center joint 196 that includes collars 198 and 199. Coil 192 is rigidly connected to a side of collar 198 from where it extends radially outwardly and then spirals inwardly until at an inner part of the spiral, it bends toward the center. At the center, there is a bent end that can extend through collar 198 to hold it in place. In this case, the interior end of the loop has a bent end for engaging the collar, but it could have the reverse form with the inner end of the spiral connected to the collar and the outer end of the spiral curved to extend through the collar. Coil 194 in this embodiment is similarly connected to the other side of the device, although the different coils can have different structures.

FIG. 20 shows device 190 of FIG. 19 with the inner ends of the coils detached from the respective collars.

Figure 21:
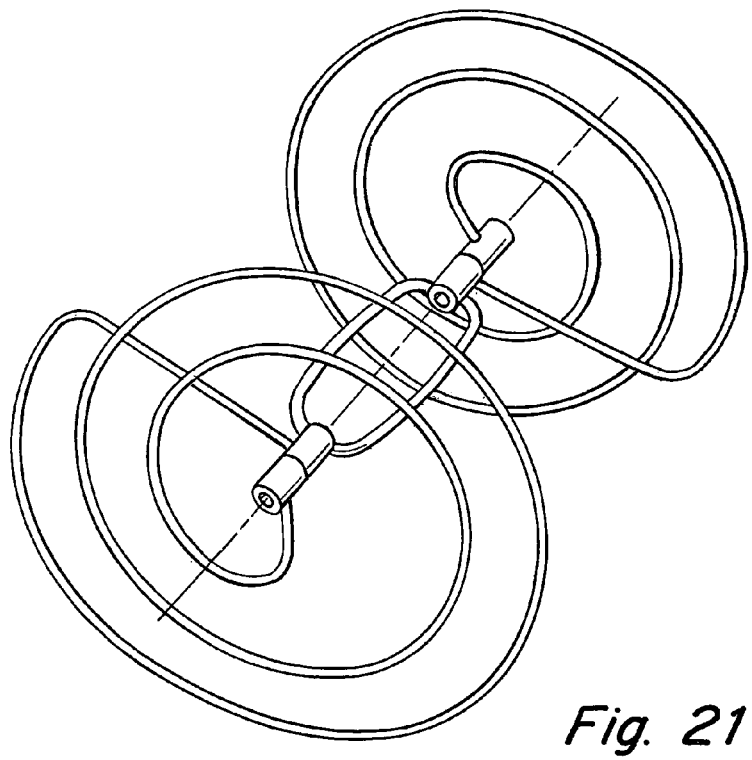
Figure 22:
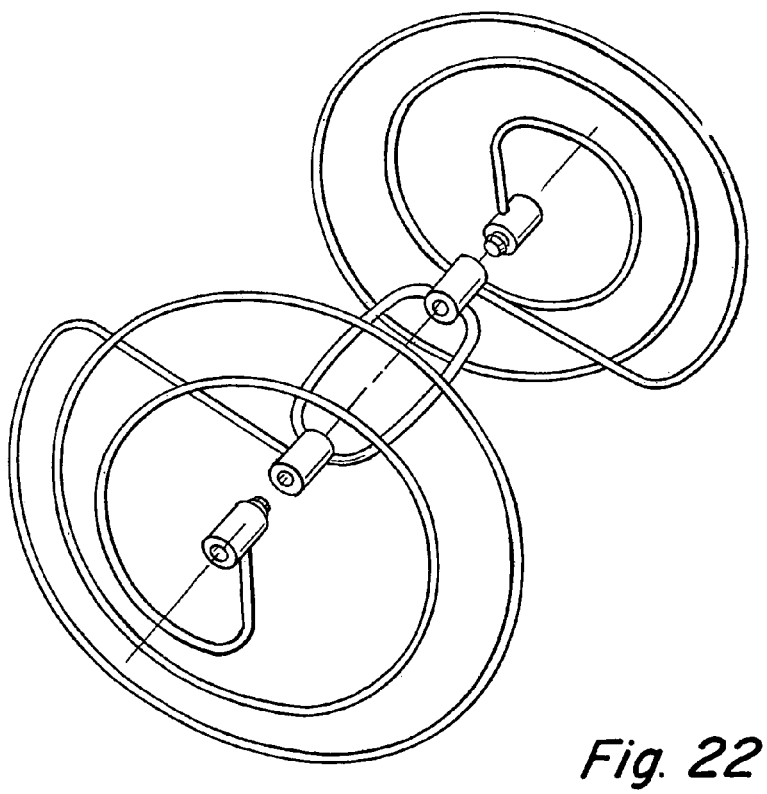

FIGS. 21 and 22 show embodiments similar to those in FIGS. 19 and 20, except that the connection between the spiral and the center joint has a snap fit to hold them together. The device is shown with the center joint and spiral detached in FIG. 22. In this case, like the embodiment of FIGS. 19 and 20, the coil spirals inwardly from the outside to a lock, but it could have the reverse form of spiral.

FIGS. 23-26 show the delivery of a device of the type shown in FIGS. 21 and 22. FIG. 23 shows the device of FIG. 21 loaded into a sheath 230, and coupled to a mandrel 240 and a delivery catheter 242. As shown herein, the device has a small profile, preferably small enough to fit in a 10 F sheath. Referring to FIG. 24, sheath 230 with the loaded device is provided through the PFO tunnel and into the left atrial side. Sheath 230 is then retracted while an end cap 234 of distal coil 232 is held in place by mandrel 240 to allow a distal coil 232 and end cap 234 to be released from sheath 230. A proximal end cap is held in place with delivery catheter 242.

Figure 25:
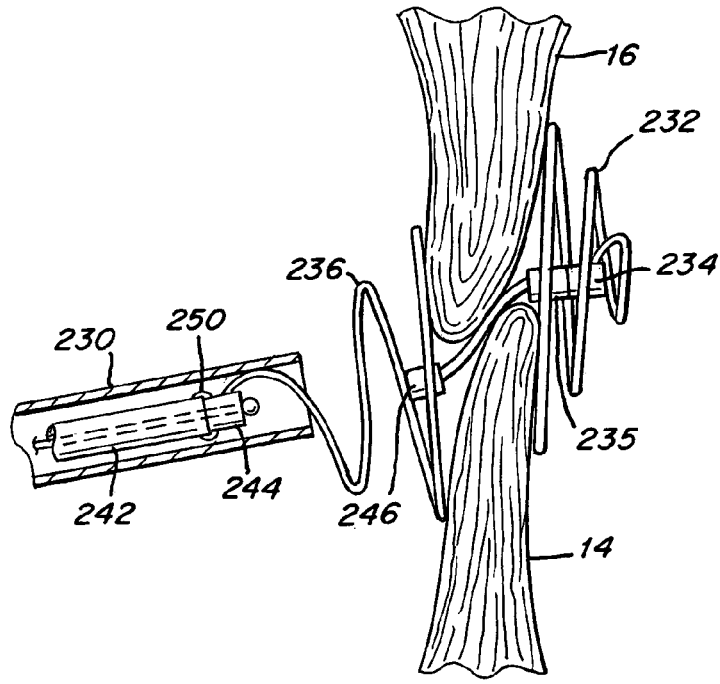
Figure 26:
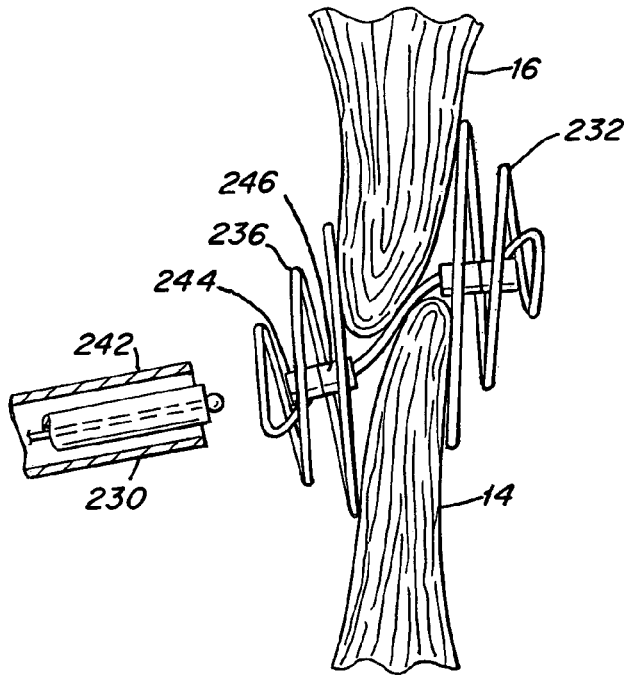

Referring to FIGS. 25 and 26, end cap 234 coupled to collar 235, e.g., with a snap fit, and mandrel 240 (not shown here) is withdrawn. Sheath 230 is then further retracted to release a proximal coil 236 against septum primum 14 and septum secundum 16 on the right atrial side until end cap 244 is coupled to collar 246. Delivery catheter 242 is releasably detached from end cap 244, resulting in the positioned device as shown in FIG. 26. The releasable connection between catheter 242 and end cap 244 can be with grappling hooks 250 (FIG. 25), which are generally known for use in delivering medical devices.

Figure 27:
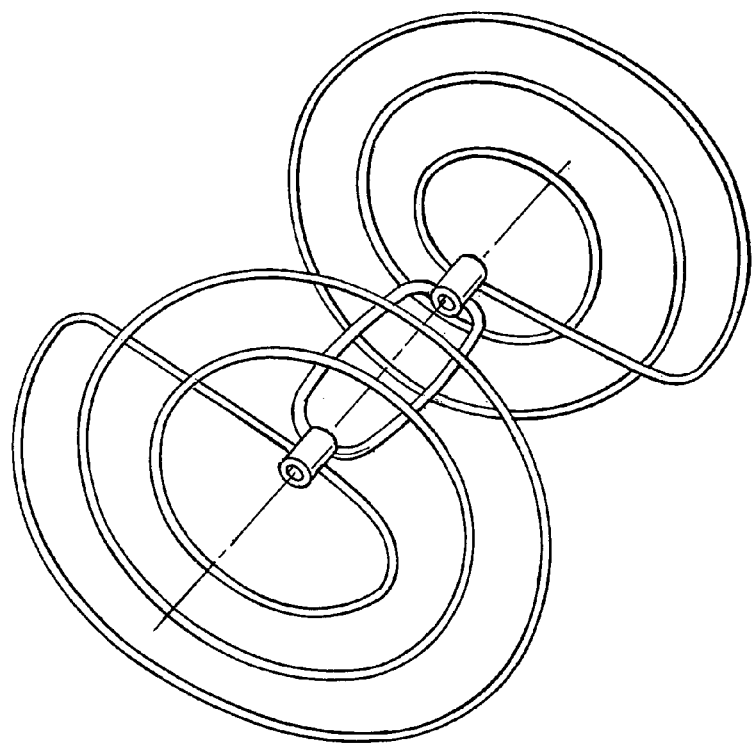
FIG. 27 is a perspective view of another embodiment of the present invention showing coils with outer ends rigidly connected to a center joint.
Figure 28:
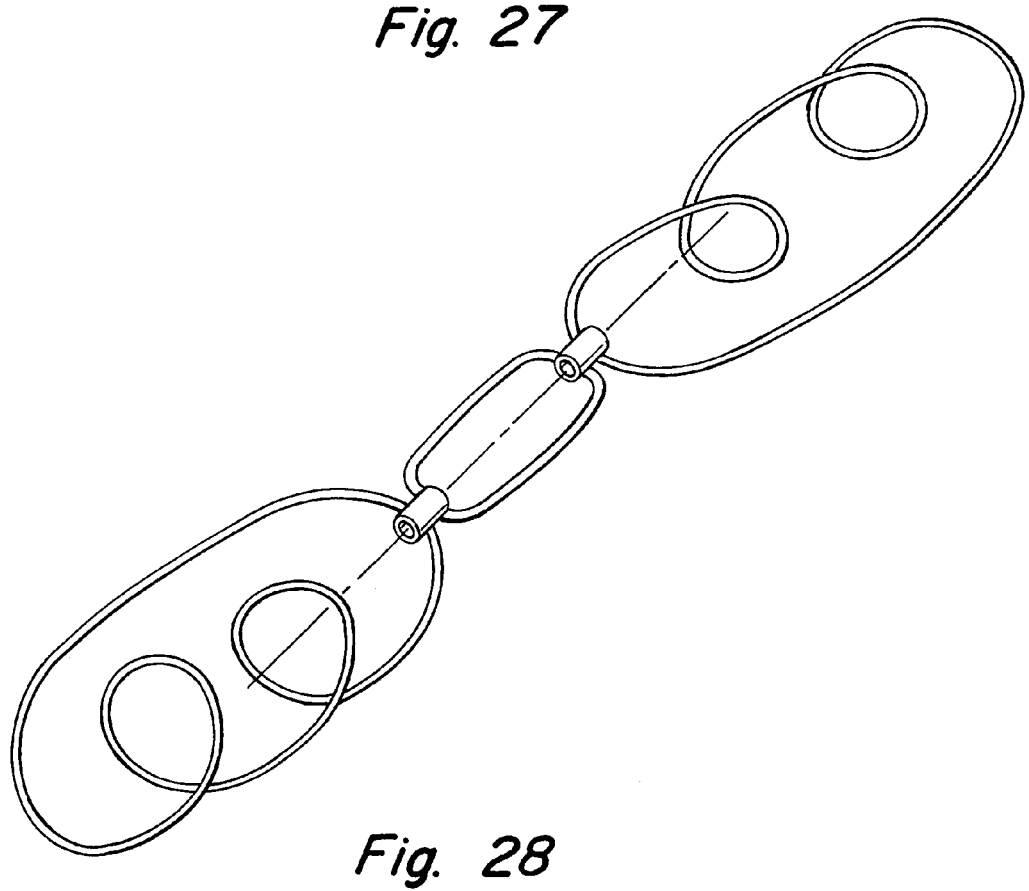
FIG. 28 is a perspective view showing the device of FIG. 27 in a partially stretched form for loading into a catheter.

FIGS. 27 and 28 show another embodiment of the present invention similar to that shown in FIGS. 21 and 22, except that the device is shown with a center joint that has a rigid and generally non-separable connection to both coils. FIG. 28 shows the device of FIG. 27 in an elongated form as it would be loaded into a sheath for delivery. With further elongation, the profile of the device can be reduced to fit inside a delivery sheath as shown in FIG. 29.

Figure 31:
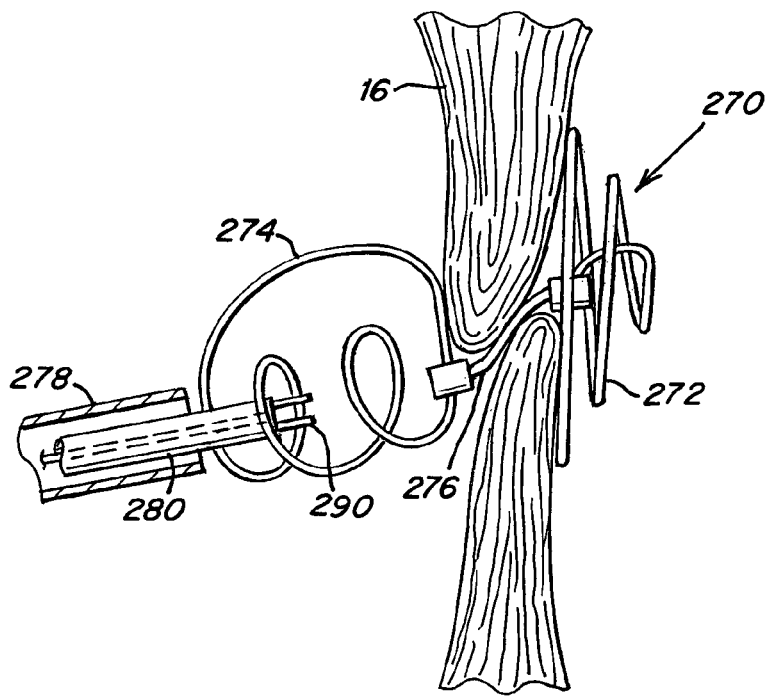
Figure 32:
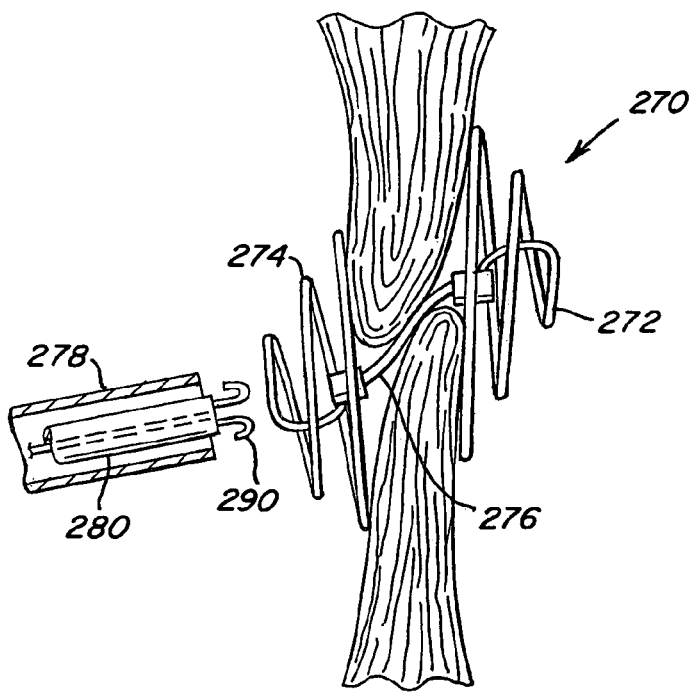

FIGS. 30-32 show the release of the device of FIGS. 27 and 28 in the PFO tunnel. This delivery is generally similar to that described in conjunction with FIGS. 23-26. A device 270 with a distal coil 272, proximal coil 274, and center joint 276 is elongated as shown in FIG. 28 and loaded into a delivery sheath 278. A first delivery catheter 280 is releasably connected to a portion of coil 274 at a proximal end, and a second delivery catheter 282 is releasably connected to a portion of distal coil 272 with a connection 284. As shown in FIG. 30, sheath 278 is withdrawn while second delivery catheter 282 holds distal coil 272 in place so it can open into a coil on the left atrial side. As shown in FIGS. 31 and 32, sheath 278 is further retracted to allow right atrial coil 274 to open on the right atrial side. Coil 274 as shown is releasably held with hooks 290 to provide control over the release. Having described embodiments of the present invention, it should be understood that modifications can be made without departing from the scope of the invention.

What is claimed:

1. A device adapted to press together the septum primum and the septum secundum between the atrial chambers, the device comprising:
   first and second clamping spirals, each having a size suitable for use on each side of the septum, wherein each of the first and second clamping spirals has a first end at an outer edge and a free end; and
   a central connector for connecting the first end of the first and second clamping spirals and passing through the tunnel between the septum primum and the septum secundum,
   wherein at least one of the spirals includes a length of wire extending in a radial direction from an inner portion of the spiral to the outer edge of the spiral and locking the free end of the spiral to the central connector.

2. The device of claim 1, wherein the spirals spiral outwardly from the central connector to the free ends.

3. The device of claim 1, wherein the central connector includes at least one hollow rod extending from a central region of the first spiral to a central region of the second spiral.

4. The device of claim 1, wherein the spirals and the central connector are formed from a single wire.

5. The device of claim 1, wherein at least one of the spirals has a radially extending portion extending from the central connector, the at least one spiral extends inwardly back to the central connector, and the center joint is flexible.

6. The device of claim 1, wherein the device is formed from a bioresorbable polymer.

7. The device of claim 1, wherein the spirals each circle around more than 360°.

8. The device of claim 1, wherein the central connector includes a scaffold for promoting tissue growth.

9. The device of claim 1, wherein the first end of each of the first and second spirals includes a radial portion connected to the central connector.

10. The device of claim 1, wherein the central connector has an opening at least one end, and the free end of at least one of the spirals is adapted to extend through the opening to form a connection.

11. The device of claim 9, wherein the central connector and the second end have a snap-fit connection.

12. The device of claim 1, wherein the first spiral spirals outwardly from the central connector and extends from an outermost point radially back to the central connector where the radial portion is connected to the central connector.

13. The device of claim 12, wherein the radial portion is detachably connected to the central connector.

14. The device of claim 12, wherein the radial portion is non-detachably connected to the central connector.

15. A device adapted to be disposed in a patent foramen ovale tunnel and comprising first and second separate spirals and a connecting member together connected to the spirals with respective first and second joints, wherein each spiral has one end at an outer edge connected to one of the first and second joints, and a second end connectible to the respective first or second joint, the spirals forming closed loops when the second end is connected.

16. The device of claim 15, wherein the spirals spiral outwardly from the first and second joints and have a radial portion extending inwardly from an outermost part of a spiral.

17. The device of claim 15, wherein the connecting member includes two wires extending between the first and second joints.

18. The device of claim 15, further comprising a membrane attached to the connecting member for promoting tissue growth.

19. The device of claim 15, wherein the first and second joints have an opening for the second end to extend through.

20. The device of claim 15, wherein the first and second joints have snap fit connectors for connection to the respective second ends.

21. A method comprising introducing into a patent foramen ovale (PFO) the device of claim 1.

22. The method of claim 21, wherein the introducing includes first providing a wire into the body, and then providing the device over the wire.

23. The method of claim 22, wherein the method includes loading the device into a sheath, providing a catheter to limit movement of the device in the proximal direction, and providing the catheter, device, and sheath to the region near the PFO.

24. The method of claim 23, further comprising extending the sheath and device through a PFO tunnel to a left atrium, limiting movement of the device in the proximal direction, and withdrawing the sheath in the proximal direction to release the second spiral on the left atrium side of the PFO.

25. The method of claim 24, further comprising further withdrawing the sheath in the proximal direction.

* * * * *